United States Patent [19]

Bruzzese et al.

[11] Patent Number: 4,784,988
[45] Date of Patent: Nov. 15, 1988

[54] PEPTIDES CORRELATED TO LYSOZYME

[75] Inventors: Tiberio Bruzzese; Armando Cedro; Holger H. Van Den Heuvel, all of Milan, Italy

[73] Assignee: Spa Societa' Prodotti Antibiotici S.p.A., Milan, Italy

[21] Appl. No.: 940,359

[22] Filed: Dec. 11, 1986

[30] Foreign Application Priority Data

Dec. 11, 1985 [IT] Italy .................. 23165 A/85

[51] Int. Cl.$^4$ .................. A61K 37/02; C07K 5/08; C07K 7/08; C07K 7/06
[52] U.S. Cl. .................. 514/14; 514/15; 514/16; 514/17; 514/18; 530/326; 530/327; 530/328; 530/329; 530/330; 530/331
[58] Field of Search .................. 530/324, 327, 313, 326, 530/327, 328, 329, 330, 331; 514/14, 15, 16, 17, 18

[56] References Cited

U.S. PATENT DOCUMENTS 4,668,663  5/1987  Boger .................. 530/327
4,677,193  6/1987  Rivier et al. .................. 530/313
4,683,221  7/1987  Weigle et al. .................. 530/327
4,683,291  7/1987  Zimmerman et al. .................. 530/324

Primary Examiner—Delbert R. Phillips
Attorney, Agent, or Firm—Oblon, Fisher, Spivak, McClelland & Maier

[57] ABSTRACT

A peptide made up of at least 3 amino acids comprised in sequential form in the following structure:

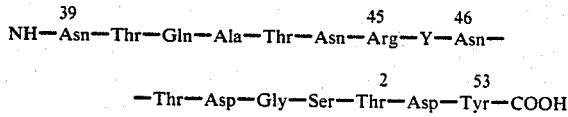

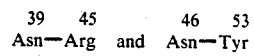

where Y may be absent or represent a glycine residue, where the amino acids $$\overset{39}{\text{Asn}}-\overset{45}{\text{Arg}} \quad \text{and} \quad \overset{46}{\text{Asn}}-\overset{53}{\text{Tyr}}$$

represent the sequences between positions 39-45 and 46-53 of hen egg-white lysozyme.

14 Claims, No Drawings

PEPTIDES CORRELATED TO LYSOZYME

DESCRIPTION

The present invention refers to peptides derived from hen egg lysozyme, their methods of preparation and pharmaceutical forms containing such peptides.

The lysozyme extracted from hen egg-white is a small globular protein made up of 129 amino acid residues of which the identity and sequence has been precisely determined.

In relation to the high content of lysine and arginine, lysozyme has a decidedly basic character, with isoelectric point around 10.5-11 and forms hydrosoluble salts with numerous inorganic and organic acids, in particular hydrochloride.

The lysozyme molecule is folded on itself and stabilized in such conformation by 4 disulfide bridges: such structure largely explains the relatively high stability of lysozyme, even in solution at pH quite distant from neutrality (in particular in acid ambient) and at moderately high temperatures. The compact conformation of the molecule is however interrupted by a side cavity which represents the active site with which the substrate must come into contact in order that the lysozyme may carry out its typical enzymatic activity: lysozyme is in fact able by a hydrolytic mechanism to selectively split the β glucoside bonds (1→4) between N-acetylmeramic acid and N-acetylglucosamine of the mucopolysaccharides, fundamental constituents of the bacterial cell membrane, and to carry out, thereby, an efficacious bacteriolytic action, even though its spectrum of action is relatively limited. Considering the mechanism and site of action described, it is obvious to conclude that the antibacterial action of lysozyme is subordinate to the integrity of its structure, even in a tridimensional sense, in a way that derangements in the molecular order do not hinder the accessibility and the direct adhesion of the mucopolysaccharide substrate of the bacterial membrane.

It is known that apart from the primary characteristic muramidase action above mentioned, lysozyme possesses other important pharmacobiologic and therapeutic activities and that its biological versatility has led to its vast employment in the clinical field. Indeed, lysozyme, for example, is endowed with a marked antiviral activity and has been used for a long time in therapy for the treatment of herpetic virus infections; it is able to interfere in the immune response as modulating agent, through an interaction on the various components of the immune system such as B-lymphocytes, helper and suppressor T-lymphocytes and macrophages, such as to condition their state of continual equilibrium; it has an already defined role in the control of membrane alterations and, in particular, of those associated with neoplastic transformations; it appears able to limit the accumulation of polymorphonuclear leukocytes in the inflammatory site with a role of modulator in such pathologic forms; it is endowed with an evident analgesic action demonstrated experimentally (limiting the abdominal contractions induced by irritants in mice and rats or raising the painful threshold of the paw), and clinically, where it proved particularly useful in reducing the pain in cancerous states.

We have found that a series of peptides expressible in terms of fragments of the lysozyme chain possess some important biological and therapeutic properties even higher that those of lysozyme itself. The peptides to which the invention refers are made up of at least 3 amino acids comprised in sequential form in the following structure:

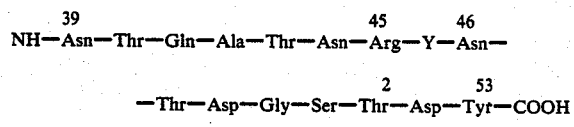

where Y may be absent or represent a glycine residue, where the amino acids

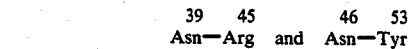

represent the sequences between positions 39-45 and 46-53 of hen egg-white lysozyme.

A particularly important peptide of the invention is pentadecapeptide made up of the L-amino acids in sites 39 to 53 of the lysozyme molecule, to which is due the following structure (I):

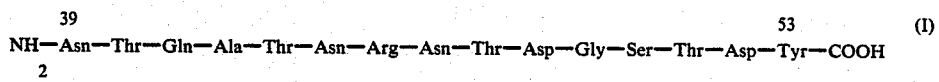

The products of the invention are obtainable either by selective fragmentation of lysozyme or by an easy synthetic route.

Such fragmentation to give active peptides may be obtained by submitting lysozyme to a hydrolytic action, induced by enzymatic substances such as pepsin or trypsin and chymotrypsin, or intervening with both enzymatic systems in succession. In all cases procedure is carried out in controlled reaction conditions and such as to orientatively simulate the predominating hydrolytic processes in vivo by action of the gastric and enteric juices respectively. The peptide mixtures thereby obtained may, in view of their biologic activity, be used as such, or after suitable purification and fractioning, or by isolating from them the peptides of the invention at the pure state. Obviously the purified and fractioned peptide mixtures and the isolated single peptides, if obtained after preliminary hydrolytic attack by the pepsin, may then be further hydrolysed with trypsin and/or chymotrypsin and then submitted to further fractioning. The peptides of the invention may also be usefully reproduced by synthetic route through sequential synthesis.

Going into details of the fragmentation procedure to prepare the abovementioned peptide mixtures and peptide (I), lysozyme is treated, for example, with pepsin (up to 20% of its weight) in a clearly acid ambient (pH 1-2.5), obtained for example by the addition of hydrochloric acid, eventually in presence of mineral salts, e.g. sodium chloride. Hydrolysis is carried out for a few hours at 30°-45°, usually at 37°-40°, then after neutralization the undissolved matter is filtered and the solution is evaporated dry or lyophilized obtaining the peptic hydrolysate "in toto" in the form of a complex mixture of peptides. Such hydrolysate, instead of being dried or lyophilized, may be fractioned by precipating the solution with acetone and, after optional purification with ethanol, by preliminary chromatography of the precipitate on silica gel (eluent water and then aqueous acetic acid up to 10-20%), followed by chromatography on weak cationic resin, for example on Amberlite CG-50 (eluent, water) to obtain thereby, as demonstrated in Scheme I, the desired peptide (I), as well as various partially purified peptide mixtures. The purification from small quantities of inorganic salts eventually present (NaCl) may be carried out by chromatography on molecular sieves such as Sephadex G 10.

SCHEME I

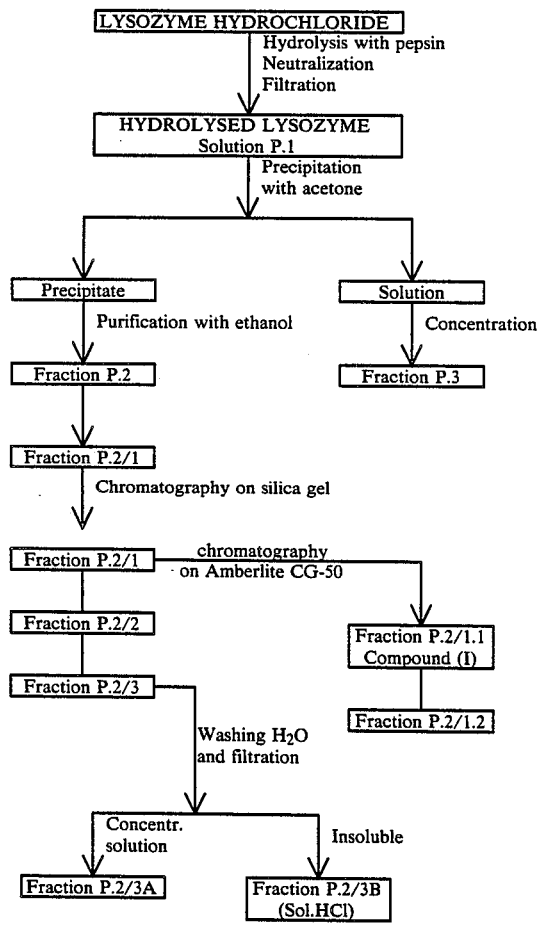

Other peptides of important biological interest are octapeptide (II) and heptapeptide (III), made up of the L-amino acids of lysozyme in sites 46-53 and 39-45 respectively, and therefore having the following structures:

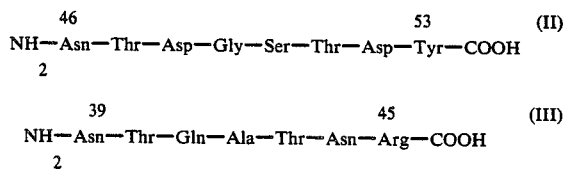

Such compounds (II) and (III) may be prepared by hydrolysis of the abovementioned peptide (I) using trypsin or chymotrypsin-trypsin (up to 5% of the weight of (I)), working in neutral or weakly basic ambient (pH 7-8.5) obtained by the addition of ammonia or suitable buffer mixture. Hydrolysis is over in a few hours at a temperature around 37° C., the solution is cooled, concentrated in small volume and subjected to chromatography to separate the two components (II) and (III), e.g. in a silica gel column, eluent ethanol/ammonia to obtain the peptide (II) and then water to isolate the peptide (III).

The abovementioned compounds may alternatively also be obtained by sequential synthesis in solid phase, inserting a few variations respect to the general procedure reported in literature for peptides in general. For example, to obtain the peptide (II) a copolymer styrenedivinylbenzene chloromethylate (Merrifield's peptide resin 1% cross-linked) is esterified with the amino acid that will be present at the carboxylic extremity of the resulting peptide, i.e. L-tyrosine (Tyr), using one of its N,O-protected derivatives, for example, N—t-ert. butoxycarbonyl (BOC)-O-benzyl-L-tyrosine, preferably in the form of cesium salt. The resulting BOC-O-benzyl-L-tyrosine-resin is isolated by filtration and washed, determining the degree of esterification with the tyrosine derivative in mmol/g resin. The group N-protective (BOC) is then removed by treatment with trifluoroacetic acid (TFA) and then the base made free by triethylamine, thereby obtaining the solid phase made up of O-benzyl-L-tyrosine-resin ready for the attack of the second amino acid constituting the desired sequence (II), i.e. L-aspartic acid (Asp).

In order to proceed to this second phase, the L-aspartic acid is utilized, as we have seen for the previous amino acid (Tyr), in protected form on functional groups not involved in the reaction, for example like BOC-L-aspartic 4-benzylester. Using an excess of reagent 2-4 times the molar quantity and using as condensation agent for the formation of the CO—NH peptide bond, for example N,N'-dicyclohexylcarbodiimide (DCCD), it is possible to obtain with very high yields the dipeptide desired which is deprived of the N-protective group (BOC) with TFA as described above, to give the (4-benzylester)Asp-(O-benzyl)Tyr-resin suitable for a successive condensation.

Working in succession, in the phases of condensation, with the following L-amino acids adequately protected:
BOC-O-benzyl-L-threonine
BOC-O-benzyl-L-serine
BOC-glycine
BOC-L-aspartic acid 4-benzylester
BOC-O-benzyl-L-threonine
BOC-L-asparagine p-nitrophenylester
and alternating now and again, as described above, the N-deprotection phases to free the amine group necessary to the successive condensation, it is possible to arrive at the peptide sequence desired tied in form of ester to the resin in solid phase.

Naturally the last amino acid considered, BOC-L-asparagine p-nitrophenylester, does not require the presence of dicyclohexylcarbodiimide (DCCD) in the condensation phase, since the carboxyl results already activated through esterfication with p-nitrophenol; advantages in terms of yield are however obtained by operating in presence of catalysts, for example 1,2,4-triazole which is able to convert the reagent into the corresponding highly reactive triazolide.

Having obtained the desired peptide sequence, it is then necessary to proceed with the splitting from the solid support and deprotection of the residual functional groups, which is carried out by action of gaseous hydrobromic acid on the peptide-resin suspension, working in trifluoroacetic acid and in presence of adequate quantities of anisole. After filtration of the resin, the solution in TFA is concentrated under vacuum and the residue, after treatment with alkalis, e.g. triethylamine, in order to deprotonize the amine group, subjected to purification to give the required peptide (II) as colorless, crystalline solid, very soluble in water.

It is important to observe that the described phase of peptide splitting from the resin (and the simultaneous phase of deprotection of the functional groups) may be carried out not only after formation of the octapeptide (II)-resin, but also after a minor number of amide condensations, and therefore also the obtaining of shorter peptides of the following structures falls within the object and the aims of the present invention:

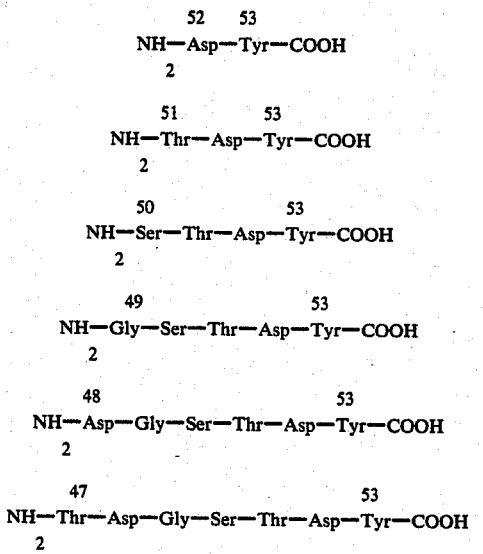

which also represent significant fractions of the lysozyme molecule.

As regards the preparation of the peptide (III), it is possible as a rule to follow the procedure described above for (II), but some important modifications must be introduced in order to arrive at the desired product. Firstly, the direct bond of arginine (N-BOC-$N_\omega$-tosyl-derivative), first amino acid at the carboxylic extremity of (III), with the chloromethyl-resin already described is seen to be very stable and can hardly be split with the HBr/TFA method of treatment: this point has been confirmed both on the Arg-resin initial ester and on the peptide (III)-resin final product. Therefore, a first modified method was devised, whereby synthesis is started with a suitable N-protected amino acid, e.g. BOC-glycine in the form of cesium salt, which is directly esterified with the chloromethyl-resin, so as to constitute an easily split "spacer" at the end of the synthesis sequential cycle. After N-deprotection by TFA, condensation is carried out in sequence with the following adequately protected amino acids:

BOC-$N_\omega$-tosyl-L-arginine
BOC-L-asparagine-p-nitrophenylester
BOC-O-benzyl-L-threonine
BOC-L-alanine
BOC-L-glutamine p-nitrophenylester
BOC-O-benzyl-L-threonine
BOC-L-asparagine p-nitrophenylester alternating as usual every phase of condensation with the relative N-BOC-deprotection phase with TFA suitable to free the α-amino group of the amino acid inserted. Proceeding as already described, every condensation phase must be carried out in presence of condensants such as N,N'-dicyclohexylcarbodiimide if the carboxyl of the amino acid is free (Arg, Thr, Ala), whereas when using the amino acids in form of p-nitrophenylesters (Asn, Gln), already highly reactive as such, it is opportune to work in presence of catalysts only, like 1,2,4-triazole.

At the end of the various condensation phases, one proceeds, by HBr in TFA, with the detachment of the peptide from the resin and with the partial deprotection of the functional groups, completing this latter operation by splitting of the $N_\omega$-tosyl radical of arginine by sodium in liquid ammonia to obtain thereby the (III)-Gly peptide compound of the following structure:

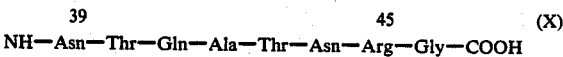

It was then possible to proceed with the detachment of the glycine by enzymatic hydrolysis with carboxypeptidase A, which resulted selectively active in splitting the carboxyterminal aminoacid whereas it is totally inactive in hydrolytic sense on the successive amino acid (Arg). Successive purification of the hydrolysis mixture by chromatography on silica gel then permitted obtaining the desired peptide (III) in substantially pure form.

Still concerning the preparation of (III), a second more direct working method was then found whereby the expected N-BOC-$N_\omega$-tosyl-arginine (cesium salt) is esterified to the chloromethyl-resin. After the successive alternating phases of N-BOC-deprotection and condensation with the above-listed amino acids, it was found that the final peptide could easily be split from the resin and completely deprotected by action of liquid hydrogen fluoride; after evaporation under vacuum of HF, extraction with trifluoroacetic acid, filtration of the resin and evaporation of the solution obtained, (III) was isolated.

The use of hydrofluoric acid as reagent therefore proves useful in many senses: it renders the use of the already discussed "spacers" (e.g. Gly) between peptide and resin superfluous, thereby avoiding the need for their final detachment by carboxypeptidase A, and moreover it permits deprotecting arginine at the same time, with spontaneous splitting also of the $N_\omega$-tosyl group, thereby rendering superfluous the next phase of deprotection by treatment with sodium in liquid ammonia. Other arginine-protected derivatives, such as BOC-$N_\omega$-nitro-L-arginine, also advantageously used as an alternative to BOC-$N_\omega$-tosyl-derivative, are similarly $N_\omega$-deprotected in a unique phase during detachment from the resin.

As already discussed at the conclusion of the synthesis of (II), the preparation of the peptide (III) may also be suspended at intermediate phases of the sequential condensation of the varius amino acids: thus, proceeding with the method involving use of spacers, it is possible to obtain, after the opportune manipulations already described, the below-listed oligopeptides:

$$\underset{2}{\overset{44\phantom{xxx}45}{\text{NH—Asn—Arg—Gly—COOH}}} \quad \text{(XI)}$$

$$\underset{2}{\overset{43\phantom{xxxxx}45}{\text{NH—Thr—Asn—Arg—Gly—COOH}}} \quad \text{(XII)}$$

$$\underset{2}{\overset{42\phantom{xxxxxxx}45}{\text{NH—Ala—Thr—Asn—Arg—Gly—COOH}}} \quad \text{(XIII)}$$

$$\underset{2}{\overset{41\phantom{xxxxxxxxx}45}{\text{NH—Gln—Ala—Thr—Asn—Arg—Gly—COOH}}} \quad \text{(XIV)}$$

$$\underset{2}{\overset{40\phantom{xxxxxxxxxxx}45}{\text{NH—Thr—Gln—Ala—Thr—Asn—Arg—Gly—COOH}}} \quad \text{(XV)}$$

and from these, after hydrolytic splitting of the glycine, by carboxypeptidase A, the corresponding peptides (XVI)–(XX):

$$\underset{2}{\overset{44\phantom{xxx}45}{\text{NH—Asn—Arg—COOH}}} \quad \text{(XVI)}$$

$$\underset{2}{\overset{43\phantom{xxxxx}45}{\text{NH—Thr—Asn—Arg—COOH}}} \quad \text{(XVII)}$$

$$\underset{2}{\overset{42\phantom{xxxxxxx}45}{\text{NH—Ala—Thr—Asn—Arg—COOH}}} \quad \text{(XVIII)}$$

$$\underset{2}{\overset{41\phantom{xxxxxxxxx}45}{\text{NH—Gln—Ala—Thr—Asn—Arg—COOH}}} \quad \text{(XIX)}$$

$$\underset{2}{\overset{40\phantom{xxxxxxxxxxx}45}{\text{NH—Thr—Gln—Ala—Thr—Asn—Arg—COOH}}} \quad \text{(XX)}$$

Proceeding viceversa by direct condensation of the arginine to the resin, it is possible to diectly arrive at the above-mentioned peptides (XVI)–(XX). As before, the numeration represents the position of the amino acid in the lysozyme structure.

A further extension of the above-described peptide syntheses permits uniting in sequential form the two procedures reported for (II) and (III): hence, initially the synthesis of (II) is reproduced as reported above, but after the usual condensation of Asn, last amino acid at the amine extremity of the peptide (II) (present in site 46 of the lysozyme molecule), instead of proceeding with the detachment of the peptide from the resin and with the deprotection of the functional groups, two alternative procedures may be followed: for example one may carry out directly the condensation of Arg, first amino acid at the carboxylic extremity of the peptide (III) (present in site 45 of the lysozyme molecule). In this case, proceeding in order with one or more reagents among those already reported for the synthesis of (III) and using the same procedures, it is obviously possible to obtain the following additional peptides, included therein (I) already obtained by enzymatic action starting from lysozyme itself:

$$\underset{2}{\overset{45\phantom{xxx}53}{\text{NH—Arg—Tyr—COOH}}} \quad \text{(XXI)}$$

$$\underset{2}{\overset{44\phantom{xxxxx}53}{\text{NH—Asn—Tyr—COOH}}} \quad \text{(XXII)}$$

$$\underset{2}{\overset{43\phantom{xxxxx}53}{\text{NH—Thr—Tyr—COOH}}} \quad \text{(XXIII)}$$

$$\underset{2}{\overset{42\phantom{xxxxx}53}{\text{NH—Ala—Tyr—COOH}}} \quad \text{(XXIV)}$$

$$\underset{2}{\overset{41\phantom{xxxxx}53}{\text{NH—Gln—Tyr—COOH}}} \quad \text{(XXV)}$$

$$\underset{2}{\overset{40\phantom{xxxxx}53}{\text{NH—Thr—Tyr—COOH}}} \quad \text{(XXVI)}$$

$$\underset{2}{\overset{39\phantom{xxxxx}53}{\text{NH—Asn—Tyr—COOH}}} \quad \text{(I)}$$

Alternatively it is possible to condense the glycine first, then the arginine and the other above-cited amino acids to finally obtain the following peptides:

$$\underset{2}{\overset{46\phantom{xxx}53}{\text{NH—Gly—Asn—Tyr—COOH}}} \quad \text{(XXVII)}$$

$$\underset{2}{\overset{45\phantom{xxx}46\phantom{xxx}53}{\text{NH—Arg—Gly—Asn—Tyr—COOH}}} \quad \text{(XXVIII)}$$

$$\underset{2}{\overset{44\phantom{x}45\phantom{xxx}46\phantom{xxx}53}{\text{NH—Asn—Arg—Gly—Asn—Tyr—COOH}}} \quad \text{(XXIX)}$$

$$\underset{2}{\overset{43\phantom{x}45\phantom{xxx}46\phantom{xxx}53}{\text{NH—Thr—Arg—Gly—Asn—Tyr—COOH}}} \quad \text{(XXX)}$$

$$\underset{2}{\overset{42\phantom{x}45\phantom{xxx}46\phantom{xxx}53}{\text{NH—Ala—Arg—Gly—Asn—Tyr—COOH}}} \quad \text{(XXXI)}$$

$$\underset{2}{\overset{41\phantom{x}45\phantom{xxx}46\phantom{xxx}53}{\text{NH—Gln—Arg—Gly—Asn—Tyr—COOH}}} \quad \text{(XXXII)}$$

$$\underset{2}{\overset{40\phantom{x}45\phantom{xxx}46\phantom{xxx}53}{\text{NH—Thr—Arg—Gly—Asn—Tyr—COOH}}} \quad \text{(XXXIII)}$$

$$\underset{2}{\overset{39\phantom{x}45\phantom{xxx}46\phantom{xxx}53}{\text{NH—Asn—Arg—Gly—Asn—Tyr—COOH}}} \quad \text{(XXXIV)}$$

These peptides, marked by the number relative to the position of the terminal amino acids in the lysozyme protein chain, are obviously also included in the aims and in the contents of the present invention.

Naturally, as well as synthesis in the solid phase, it is possible to carry out traditional synthesis in homogeneous phase starting from the desired amino acid having the free α-amino group, the α-carboxyl group protected as benzyl ester and eventual functional groups of the side chains also suitably protected (for example the hydroxyl group of threonine or phenol group of tyrosine protected as benzyl ethers, the β-carboxyl group of aspartic acid protected as benzyl ester, the guanidine group of arginine protected by the nitro-group).

The first amino acid is made to react, in solution (homogeneous phase) with the second amino acid of the sequence having the amino group protected (e.g. like BOC), as well as the eventual functional groups of the side chain; the α-carboxyl group may instead be free, resorting therefore to the use of a condensant (e.g. DCCD) to form the peptide bond, or in the form of active ester (e.g. p-nitrophenylester or N-hydroxysuccinimide ester).

The dipeptide obtained, completely protected, is isolated, purified, BOC-deprotected with TFA/CH$_2$Cl$_2$, deprotonized with triethylamine and made to react with the third amino acid according to the previous scheme and so on until the end of the synthesis.

After isolation and BOC-deprotection, the peptide is subjected to catalytic hydrogenation with Pd on carbon for the detachment of the side chain protection groups and of the benzyl ester group that protects the first amino acid carboxyl in α.

The peptide completely deprotected is then isolated by lyophilization of the solution, after filtration of the catalyst, and suitably purified.

With regard to the biological activity of the peptide mixtures obtained by enzymatic hydrolysis of lysozyme, like many of the peptides isolated at the pure state and/or reproduced through synthesis, it is observed, as previously reported, that they lack the bacteriolytic activity typical of the integral lysozyme structure, whereas they present important pharmacological and therapeutic properties. It was therefore possible for example to evidence a marked analgesic activity of numerous peptides, by testing their anti-nociceptive effects on laboratory animals using the well-known Randall-Selitto method.

In groups of 5-10 rats, hyperalgesia of the paw is induced by administering an irritant agent, for example brewer's yeast (10 mg/rat), into the planter aponeurosis and at the same time injecting the product under test at different doses. One group of rats is treated with the irritant agent alone. At intervals, in particular after 3 hours, the painful threshold on compression of the edematous paw is measured, i.e. the minimum pressure (in g) causing the sudden withdrawal of the paw of the animal.

The results are expressed as percentage increase in the mean painful threshold compared to the paw treated with the algogenic agent alone (without the drug). As an example, the data relative to the peptide mixture denominated "Fraction P.2" of chromatographic origin (See Scheme 1) are reported, as well as the individual peptides (I), (II) and (III).

TABLE I

| | Fraction P.2 | (I) | (II) | (II) | (II) | (III) | (III) | (III) |
|---|---|---|---|---|---|---|---|---|
| Dose (mg/rat) | 2 | | 2 | 0.5 | 0.75 | 1 | 1 | 2 | 4 |
| Δ% of the algogenic threshold | 70 | 120 | 30 | 60 | 90 | 30 | 60 | 100 |

Analogous results were obtained in other tests carried out with different irritant agents such as carrageenan, kaolin and arachidonic acid and even when the above peptides were used by systemic routes, including intramuscular, intravenous and oral. Unlike local administration in the inflamed paw, the use of the substance by systemic route in the laboratory animal obviously entails much higher dosages ranging from 10 to 200 mg/kg. With regard to the single peptides, perfect analogy was found between samples isolated from the product of enzymatic hydrolysis of lysozyme and the corresponding peptides obtained by synthetic route.

Yet other example, the mixture and the peptides of the present invention resulted active in an antiviral sense in numerous cases. They were submitted to various tests to verify their influence on the capacity of the herpes simplex virus to infect and form plaques on monolayer cell cultures. To this purpose, a viral strain of herpes simplex Type 1 at suitable concentration was added to monolayers of Vero cells (Flow). After being in contact for 1 hour, the virus was removed and the monolayer washed and then covered with fresh culture medium T199 (Flow), adding at the end suitable quantities of the substance under test. After 72 hours' incubation, the plates were coloured with neutral red and the visible plaques counted. In this test, the P.2 fraction (Scheme I), obtained by hydrolysis of lysozyme with pepsin, was seen at the concentration of 5 mg/ml to be able to inhibit the viral capacity to form plaques by 95%, thereby demonstrating an anti-herpetic activity, much higher than lysozyme itself in integral form (75% inhibition at the same concentration). Similar results were obtained with a peptide fraction isolated in an analogous manner after hydrolysis of lysozyme with trypsin and chymotrypsin. Even more surprising results were obtained with peptides such as (I) or (III) which resulted capable of inducing analogous reductions in the viral plaque-forming units at considerably lower concentrations (0.1-1 mg/ml). Moreover, these peptides did not influence the cell colony-forming capacity and were therefore seen devoid of cytotoxic effects, even at much higher concentrations than those active in an antiviral sense.

A further example of the biological effects discovered for the compounds of the present invention, is their ability to interfere with the immune system by a modulating action: some peptides were in fact seen to be able to modify the quantity of bovine anti-albumen antibodies after administration of this antigen in mice or also to increase the number of plaque-forming cells on erythrocytes of sheep in the spleens of mice inoculated with ram red blood cells. Herebelow reported are some preparative examples, without however limiting to them the importance and the aims of the present invention.

EXAMPLE 1

Enzymatic hydrolysis (pepsin) of lysozyme

Under stirring add 8 g of pepsin and 5 g of sodium chloride to 1 liter of distilled water previously heated at 40° C., bringing to pH 1.2 by adding 37% hydrochloric acid.

Dissolve 50 g of lysozyme chloride in the solution thus obtained, bring to pH 1.2 and keep under slow stirring at 40° C. in a thermostated bath for 1 hour. Bring to pH 7 with 30% sodium hydroxide, eliminate the slight precipitate formed by filtration and bring the solution to dryness by careful distillation under vacuum or by lyophilization.

EXAMPLE 2

Enzymatic hydrolysis (trypsin-chymotrypsin) of lysozyme

Dissolve 50 g of lysozyme hydrochloride in 1 liter of distilled water, bring to pH 8 by addition of diluted ammonia, then add 5 g of trypsin-chymotrypsin complex and again adjust the pH to 8. Keep the solution obtained at 37° C. for 2 hours (analogous results are obtained also by prolonging heating up to 12 hours) and then evaporate dry by careful distillation under vacuum or by lyophilization.

EXAMPLE 3

Fractioning of the peptides by hydrolysis with pepsin and isolation of the peptide (I) (Scheme I)

(A) Precipitation with acetone. Keep the final solution obtained according to the procedure in Example 1 (Solution P.1, volume about 1 liter) under stirring and treat directly, before evaporating to dryness, with 4 liters of acetone. Leave the very dense oily phase formed to sediment, while concentrate the clear aqueous-acetone solution to dryness under vacuum thereby making up the P.3 fraction: this is a peptide mixture containing also almost all of the sodium chloride used in the hydrolysis phase in Example 1.

Disintegrate the dense oily phase with 500 ml of ethanol thereby obtaining, after prolonged agitation, a colorless, crystalline solid which is collected by filtration and dried at 40° under vacuum to give 30 g of peptide mixture (P.2 fraction).

(B) Chromatography on silica gel. Dissolve the P.2 fraction thus obtained in 100 ml of distilled water and submit to column chromatography on 450 g of silica gel 60 (70–230 mesh), using distilled water as first eluent. By controlling the absorption at ultraviolet light ($\lambda=281$ nm) on the eluate and thin layer chromatography (TLC) on silica gel 60 F254 (eluent n.butanol:water:acetic acid 100:30:10, detector ninhydrin) a first fraction is isolated (TLC, Rf=zero), which is evaporated dry under vacuum giving about 7 g of P.2/1 fraction. By continuing the elution of the chromatographic column with a mixture water:acetic acid: 98:2, the P.2/2 peptide fraction (7.5 g) is obtained by concentration to dryness whereas with water:acetic acid 90:10 the last fraction P.⅔ is recuperated as peptide mixture (8 g). This latter fraction is then advantageously purified first by extraction with water (recuperating the P.⅔A fraction from the solution by concentration) and then with hydrochloric acid (P.⅔B fraction).

(C) Chromatography on Amberlite CG-50. The above-described P.2/1 fraction, obtained on silica gel by elution with water, is further purified by chromatography on ion-exchange resin, using 450 ml of Amberlite CG-50 in acid form. By eluting with distilled water and reuniting the eluates according to the absorption peaks at ultraviolet light ($\lambda=281$ nm) and thin layer chromatography on silica gel 60 F 254 (eluent n.butanol:water:acetic acid 100:30:10, detector ninhydrin), fraction P.2/1.1 is isolated first (Rf zero), which by evaporation to dryness gives 1.8 g of compound (I) (peptide 39–53 of lysozyme), and then fraction P.2/1.2 made up of a mixture with other peptides.

| Mmol | Analysis: Amino acids of the fraction P.2/1.1 [peptide (I)] after total hydrolysis: | | | | | | | | |
|---|---|---|---|---|---|---|---|---|---|
| | Ala | Arg | Asp | Glu | Gly | Ser | Thr | Tyr | (NH$_3$) |
| Expected | 1 | 1 | 5 | 1 | 1 | 1 | 4 | 1 | (4) |
| Found | 1.00 | 1.01 | 4.92 | 1.02 | 1.03 | 0.97 | 0.99 | 1.01 | (3.95) |

EXAMPLE 4

Enzymatic hydrolysis (trypsin) of the peptide (I) and isolation of peptides (II) and (III)

Dissolve 2 g of peptide (I), isolated according to the procedure in Example 3, in 400 ml of distilled water and bring the solution to pH 8 with ammonia. Add 40 mg of trypsin and heat at 37° C. for 2.5 hours. Carefully concentrate under vacuum up to a volume of about 10 ml and verify by thin layer chromatography on silica gel 60 F254 (eluent ethanol: 28% ammonia 70:30, detector ninhydrin) the disappearance of the peptide (I) (Rf 0.07) and the formation of two new spots characteristic of peptide (II) (Rf 0.3) and peptide (III) (Rf 0.15). The two products are advantageously isolated and purified e.g. by column chromatography on silica gel 60 (70–230 mesh), following the elution of the eluates by determination of the ultraviolet absorption ($\lambda=281$ nm) and in particular by TLC control carried out as described above. Then load the concentrated hydrolysis solution into a chromatographic column containing 200 g silica gel, eluting first with a mixture of ethanol:28% ammonia 95:5 to remove small quantities of impurities and then with a mixture of ethanol:28% ammonia 8:2 from which, by concentrating the eluates to dryness under vacuum, 640 mg of peptide (II) is obtained. Then carry out elution with a mixture of ethanol: 28% ammonia 7:3, discarding the corresponding eluates, and then with distilled water only obtaining, by evaporating dry, 460 mg of peptide (III).

The hypothesis that the trypsin had split the peptide bond of (I) between the arginine carboxyl and the amine group of the adjacent amino acid (asparagine) to give (II) (peptide made up of the lysozyme amino acids 46–53) and (III) (peptide made up of the lysozyme amino acids 39–45), is supported by the further examination of their eluates: (II) has elevated UV absorption at 281 nm and is detected in TLC with Pauly's reagent (presence of tyrosine) whereas it is not detected with Sakaguchi's reagent (absence of arginine); (III) has a contrary behavior at the UV examination and TLC in that it contains arginine but tyrosine is absent. These data are definitely confirmed by analysis of the amino acids.

| Mmol | Analysis of the amino acids after total hydrolysis | | | | | | | | |
|---|---|---|---|---|---|---|---|---|---|
| | Ala | Arg | Asp | Glu | Gly | Ser | Thr | Tyr | (NH$_3$) |
| (II): Expec.: | | | 3 | | 1 | 1 | 2 | 1 | (1) |
| Found: | | | 2.98 | | 0.99 | 1.02 | 2.01 | 1.00 | (0.98) |
| (III): Expec.: | 1 | 1 | 2 | 1 | | | 2 | | (3) |
| Found: | 1.00 | 1.02 | 1.98 | 0.99 | | | 2.01 | | (2.96) |

EXAMPLE 5

Sequential synthesis of peptide (II) in solid form (A) Esterification of the chloromethyl-resin with tyrosine and BOC-deprotection. 5 g of styrene-divinylbenzene chloromethylated copolymer (resin for peptide synthesis according to Merrifield) are esterified with 742 mg (2 mmol) of BOC-O-benzyl-L-tyrosine in presence of 0.28 ml (2 mmol) of triethylamine heating to boiling for 45 hours in 40 ml of ethyl acetate.

The resin is collected by filtration, washed thoroughly with ethyl acetate, ethanol and water, and vacuum-dried at 25° C. 5.375 g of BOC-O-benzyl-L-tyrosine-resin are thereby obtained having an esterification degree of 0.201 mmol Tyr/g of resin, determined by difference after spectrophotometric determination at 276 nm of the free tyrosine derivative (not esterified) in the reaction and washing solvents.

NOTE: Using the BOC-O-benzyl-L-tyrosine as cesium salt and carrying out the reaction in dimethylformamide for 24 hours at 50° C. (in absence of triethylamine), yields of around 0.3 mmol Tyr/g of resin are obtained.

The resin isolated as described above is then treated with 70 ml of a mixture of trifluoroacetic acid and methylene chloride 1:1 for 30 minutes in order to proceed with the BOC-deprotection. It is then filtered and treated with 70 ml of 10% triethylamine in chloroform for 10 minutes to free the amine group. After filtration and washing of the resin with chloroform and methylene chloride, the required O-benzyl-L-tyrosine-resin is then obtained.

(B) Condensation with aspartic acid and BOC-deprotection. Suspend the resin in 130 ml of methylene chloride and treat with 1050 mg (3.24 mmol), i.e. three times the equimolecular quantity, of 4-benzylester BOC-L-aspartic acid. After 10 minutes under agitation, add as condensing agent 670 mg (3.24 mmol) of N,N'-dicyclohexylcarbodiimide (DCCD) in 30 ml of methylene chloride and carry out the reaction for about 12 hours at 20° C.

The resin is collected by filtration and washed with methylene chloride and methanol, verifying the completeness of the condensation with ninhydrin (no coloration). Proceed then with the BOC-deprotection by reaction with trifluoroacetic acid and with the treatment with triethylamine according to the procedure in Example 5(A), thereby obtaining the (4-benzylester) Asp-(O-benzyl)Try-resin in a form suitable for the next condensation.

(C-G) Successive condensations and BOC-deprotections Carry on with the various condensation phases in presence of DCCD alternated with the BOC-deprotection phases according to the procedure in Example 5(B), using a three-fold quantity respect to the stoichiometry of the following protected amino acids, in the order (C) BOC-O-benzyl-L-threonine
(D) BOC-O-benzyl-L-serine
(E) BOC-glycine
(F) 4-benzylester BOC-L-aspartic acid
(G) BOC-O-benzyl-L-threonine (H) Condensation with asparagine and splitting from the resin with total deprotection. Suspend the resin coming from the reaction phase (G) and BOC-deprotected (5.0 g) in 120 ml of dimethylformamide and treat with 1530 mg (4.52 mmol), i.e. 4 times the equimolecular quantity, of BOC-L-asparagine p-nitrophenylester. Continue the condensation reaction under agitation, at room temperature for 18 hours, then collect the resin by filtration, wash with dimethylformamide and methylene chloride and vacuum-dry.

NOTE: In a variation of the procedure the p.nitrophenyl ester of the BOC-L-asparagine is advantageously activated by catalysts, e.g. 1,2,4-triazole.

The peptide-resin obtained as described above is submitted to the splitting of the peptide from the solid support and to the total deprotection of the functional groups, by suspension in 80 ml of trifluoroacetic acid containing 4 ml of anisole, and successive passing of a current of gaseous hydrobromic acid through the suspension. After slow bubbling for 80 minutes at 15° C., the resin is filtered and washed with trifluoroacetic acid and the reunited filtrates (containing in solution the split and deprotected peptide) evaporated under vacuum until a dense oily residue is obtained. By successive treatment for 1 hour with triethylamine in ethanolethyl ester a white crystalline precipitate is immediately formed which is collected by filtration and vacuum-dried, giving 612 mg of peptide (II) (overall yield: 65%, calculated on the first amino acid condensed) identical to the product isolated in Example 4.

EXAMPLE 6

Synthesis of peptides (IV)–(IX)

The various preparations are begun by esterification of the chloromethyl-resin with the first amino acid and successive BOC-deprotection according to the procedure in Example 5A, thereby obtaining the O-benzyl-L-tyrosine-resin. Carry on by condensing in the desired order, one or more of the protected amino acids described in Examples 5B–5G, inserting in the intermediate phases the BOC-deprotection of the last amino acid condensed.

After condensation of the last amino acid desired, complete the synthesis by splitting of the peptides (IV)–(IX) from the resin, and simultaneous total deprotection according to the final procedure described in Example 5H.

EXAMPLE 7

Sequential synthesis of peptide (III) in solid phase (method with spacer)

(A) Esterification of the chloromethyl-resin with glycine (spacer) and BOC-deprotection. −9.0 g of styrenedivinylbenzene chloromethylated copolymer (resin for peptide synthesis according to Merrifield) are esterified with 2500 mg (8.14 mmol) of cesium salt of the BOC-glycine by suspension in 75 ml of dimethylformamide and heating for 24 hours at 50° C. under agitation. The resin is collected by filtration, washed with dimethylformamide (DMF), DMF:water: 9:1, and ethanol and vacuum-dried giving 9.830 g of BOC-glycine-resin.

By treatment for 1 hour at 100° C. of an aliquot of resin (250 mg) with 2.5 ml of pyridine, dilution with 25 ml of 50% acetic acid, and titration according to Volhard of the residual chlorides, the degree of esterification of the resin corresponding to 0.785 mmol Gly/g of resin is obtained by difference respect to the chlorides determined on the chloromethyl resin.

The BOC-Gly-resin is then BOC-deprotected by treatment with 150 ml of TFA:CH$_2$Cl$_2$ 1:1, keeping the suspension under agitation for 30 minutes at room temperature. After filtration and washings with methylene chloride, the resin is treated with 150 ml of 10% triethylamine in chloroform, 10 minutes under agitation at room temperature, to free the salified amine group, then filtered, washed with CHCl$_3$ and CH$_2$Cl$_2$ and vacuum-dried obtaining a quantitative yield of Gly-resin.

(B) Condensation with arginine and BOC-deprotection. The Gly-resin is suspended in 200 ml of methylene chloride and treated with a triple-molar quantity respect to the glycine of the second amino acid (first amino acid of the sequence desired), adding a solution of 9.85 g (23 mmol) of BOC-N$_\omega$-tosyl-L-arginine in 60 ml of DMF:CH$_2$Cl$_2$ 1:1. After 10 minutes under agitation, 4.76 g (23 mmol) of DCCD dissolved in 30 ml of methylene chloride are added and left under agitation at room temperature for 20 hours. The resin is then filtered and washed with CH$_2$Cl$_2$ and with ethanol, then vacuum-dried obtaining 12.3 g of BOC-N$_\omega$-tosyl-L-arginine-glycine-resin which, when controlling with ninhydrin, confirms the absence of free amine groups.

The resin thereby isolated is then subjected to BOC-deprotection by treatment in suspension with 120 ml of TFA:CH$_2$Cl$_2$ 1:1, keeping under agitation at room temperature for 30 minutes. The resin is then isolated by filtration and washed with CH$_2$Cl$_2$, and then, as usual, treated with 10% triethylamine in CHCl$_3$ (100 ml), keeping under agitation for 10 minutes, to thereby obtain the required N$_\omega$-tosyl-L-arginine-glycin-resin.

(C) Condensation with asparagine and BOC-deprotection. The resin obtained as above is suspended in 100 ml of dimethylformamide, adding 10.9 g (30.8 mmol), i.e. 4 times the equimolar quantity, of BOC-L-asparagine p-nitrophenylester dissolved in 40 ml of DMF and 2.13 g (30.8 mmol) of 1,2,4-triazole dissolved in 30 ml of DMF. The reaction mixture is kept under agitation at room temperature for 120 hours, then the resin is filtered, washed with DMF, CH$_2$Cl$_2$ and ethanol, and vacuum-dried thereby obtaining the BOC-Asn(N$_\omega$-tosyl)Arg-Gly-resin. When controlling with ninhydrin, the product is seen to be devoid of free amine groups. Then BOC-deprotection is carried out by agitation at room temperature for 30 minutes in 120 ml of TFA:CH$_2$Cl$_2$ 1:1. After filtration and washing with CH$_2$Cl$_2$, the resin is suspended for 10 minutes under agitation in 100 ml of 10% triethylamine in chloroform, filtered, washed with CHCl$_3$ and CH$_2$Cl$_2$, and vacuum-dried thereby obtaining the Asn-(N$_\omega$-tosyl)Arg-Gly-resin with almost quantitative yield.

(D-E) Condensation with threonine and with alanine and relative BOC-deprotections. The above-isolated resin is condensed with BOC-O-benzyl-L-threonine and BOC-deprotected, then condensed again with BOC-L-alanine and BOC-deprotected, working in both phases as reported in Example 7B.

(F) Condensation with glutamine and BOC-deprotection. The BOC-L-glutamine p-nitrophenylester is used for the condensation phase following, in condensation and deprotection phase, the procedure reported in Example 7C.

(G) Condensation with threonine and BOC-deprotection. The condensation phase is carried out by using the BOC-O-benzyl-L-theronine and following, in condensation and deprotection phase, the procedure reported in Example 7B.

(H) Condensation with asparagine and splitting from the resin with partial deprotection. The resin isolated at the end of the procedure reported in Example 7G is further condensed with BOC-L-asparagine p-nitrophenylester following in so far as the condensation phase—the procedure reported in Example 7C and thereby obtaining the BOC-Asn-(O-benzyl)Thr-Gln-Ala-(O-benzyl)Thr-Asn(N$_\omega$-tosyl)Arg-Gly-resin. The resin thereby obtained is suspended, without going through the usual BOC-deprotection phase, in 150 ml of trifluoroacetic acid containing 4 ml of anisole, bubbling into the suspension a slow flow of gaseous hydrobromic acid. The reaction, moderately exothermic at the beginning, is over in about 60 minutes, then the resin is filtered and washed with TFA and the filtrate concentrated almost to dryness by distillation under vacuum at a temperature lower than 40° C. The oily residue is treated with triethylamine in ethanol-ethyl ether in excess, rapidly obtaining a crystalline precipitate which is collected by filtration and dried to give 4.46 of peptide NH$_2$-Asn-Thr-Gln-Ala-Thr-Asn-(N$_\omega$-tosyl)Arg-Gly-COOH.

(I) N$_\omega$-tosyl-deprotection. The above-isolated peptide is dissolved in about 450 ml of liquid ammonia at a temperature of −33° C., obtaining a clear, yellow solution. By portions 4.2 g of metallic sodium are added obtaining an intense blue coloration, persisting for at least 60 minutes, then the sodium amide in excess is destroyed by the addition of 9.6 g of ammonium chloride in portions, with consequent decoloration of the solution, and the ammonia left to evaporate. The residue is dissolved with 90 ml of water, a small quantity of insoluble material filtered away and the pH adjusted to 7 with diluted HCl. The resulting solution is chromatographed on a column containing 200 g of Sephadex G-10, eluating with distilled water and collecting the fractions devoid of chloride ions and hence inorganic salts and controlling the eluate with TLC on silica gel, eluent ethanol:28% ammonia, 7:3. The fractions obtained, by concentration under vacuum, give 3.3 g of peptide (III)-glycine (structure X).

| Analysis of the amino acids after total hydrolysis of (X): | | | | | | | |
|---|---|---|---|---|---|---|---|
| Mmol | Ala | Arg | Asp | Glu | Gly | Thr | (NH$_3$) |
| Expected | 1 | 1 | 2 | 1 | 1 | 2 | (3) |
| Found | 1.00 | 0.99 | 1.98 | 1.01 | 1.01 | 1.99 | 2.97 |

(L) Splitting of the glycine. 3 ml (equal to 75 mg) of carboxypeptidase A suspension (from bovine pancreas, Boehringer Mannheim) are diluted to 30 ml and centrifuged at 2000 revs/min for 5 minutes. The clear solution is discarded and the residue dissolved in 6 ml of 1M ammonium carbonate, pH 7.8, bringing to 30 ml with distilled water. This solution is then added to a solution of 3.3 g of peptide (III)-glycine in 300 ml of water brought to pH 8.5 with diluted ammonia. The resulting solution is kept at 37° C. and at the same pH of 8.5 for 2.5 hours under agitation, then brought to pH 6 with diluted HCl and concentrated under vacuum and at a reduced temperature up to a volume of 30 ml. The solution is then submitted to column chromatography on silica gel, eluating with ethanol:28% ammonia, in the order 95:5, 90:10 and 80:20, to remove the glycine separated during enzymatic hydrolysis. By successive elution with water, under vacuum concentration of the eluate up to small volume and successive treatment with 200 ml of ethanol, a precipitate is obtained which is collected by filtration. The product is further purified by dissolution in 120 ml of water, filtering away small quantities of insoluble matter and then percolating the solution on Sephadex G 10.

The initial fractions, controlled in TLC and verified the absence of chloride ions, are concentrated under vacuum and treated again with 200 ml of ethanol: a white crystalline precipitate is obtained which is filtered and dried giving 2.5 g of peptide (III), identical to the product isolated in Example 4.

EXAMPLE 8

Sequential synthesis of peptide (III) in solid phase (direct method)

(A) Esterification of the chloromethyl-resin with arginine and BOC-deprotection. 4.0 g of resin for peptide synthesis according to Merrifield are suspended in 40 ml of dimethylformamide and treated with 2000 mg (3.57 mmol) of BOC-$N_\omega$-tosyl-L-arginine cesium salt keeping under agitation at 50° C. for 24 hours. The resin is then filtered, washed with DMF, DMF:H$_2$O 9:1 and ethanol and vacuum-dried giving the expected BOC-$N_\omega$-tosyl-Arg-resin, with a degree of esterification equal to 0.75 mmol Arg/g of resin.

The resin obtained is then BOC-deprotected by treatment in suspension with 50 ml of TFA:CH$_2$Cl$_2$ 1:1, keeping under agitation for 30 minutes at room temperature. The resin is then collected by filtration, washed with CH$_2$Cl$_2$ and treated with 50 ml of 10% triethylamine in CHCl$_3$ keeping under agitation for 10 minutes. It is filtered, washed with CHCl$_3$ and CH$_2$Cl$_2$ and vacuum-dried obtaining the $N_\omega$-tosyl-L-Arg-resin.

(B-F) Proceed in order with the condensation of the resin obtained above with asparagine, threonine, alanine, glutamine, threonine and with the corresponding BOC-deprotections following exactly the respective preparative Examples 7C-7G.

(G) Condensation with asparagine and splitting from the resin with total deprotection. The BOC-deprotected resin obtained above in Example 8F is treated with BOC-L-asparagine p-nitrophenylester following, for the condensation phase, the procedure reported in Example 7H. Proceed with the splitting from the resin by treatment with anhydrous hydrofluoric acid and 1 ml of anisole for 1 hour at the temperature of 18°-20° C. After evaporation of the hydrofluoric acid from the reaction mixture, the peptide is separated from the resin by extraction with TFA, filtered and washed with TFA and the reunited filtrates concentrated at reduced pressure. The residue is treated with triethylamine in ethanol-ethyl ether in excess obtaining a crystalline solid which is filtered and dried. The product thereby obtained results totally deprotected and is identical to the peptide (III) obtained in Example 4 and Example 7.

NOTE: Analogous results are obtained with the alternative use of BOC-$N_\omega$-nitro-L-arginine in the initial phase of esterification in Example 8A. Such substitution does not influence the various condensation phases, nor the final phase of splitting from the resin and total deprotection reported in Example 8G.

EXAMPLE 9

Synthesis of peptides (XI)-(XV)

Esterify the chloromethyl-resin with BOC-glycine and proceed with BOC-deprotection as indicated in Example 7A.

Continue with the condensation in the order with one or more of the protected amino acids reported in Examples 7B-7G (and with the consequent BOC-deprotections) depending on the product desired. After condensation of the last amino acid desired, proceed with the splitting of the peptides from the resin and, simultaneously, with the partial deprotection, as indicated in Example 7H and, then, with the $N_\omega$-tosyl-deprotection of the arginine radical, as indicated in Example 7I, thereby obtaining the required peptides (XI)-(XV).

EXAMPLE 10

Synthesis of the peptides (XVI)-(XX)

The preparation is carried out by submitting the corresponding peptides (XI)-(XV) to the enzymatic splitting of the glycine by action of the carboxypeptidase A, according to the procedure indicated in Example 7L.

Alternatively, proceed as indicated in Example 8, esterifying the chloromethyl-resin with arginine (Example 8A), condensing in the order of the amino acids desired (Examples 8B-8F) and then proceeding with the splitting of the peptides from the resin and the simultaneous total deprotection with HF-TFA (Example 8G), to obtain the required peptides (XVI)-(XX).

EXAMPLE 11

Synthesis of peptides (XXI)-(XXVI) and peptide (I)

The methods of synthesis result to be an obvious extension of the above-reported procedures. Begin with the sequential synthesis of peptide (II) in solid phase as indicated in Examples 5A-5G.

After condensation with asparagine (lysozyme amino acid in position 46), according to Example 5H, instead of proceeding with the splitting from the resin, proceed with the further condensation with arginine (lysozyme amino acid in position 45) and with other amino acids making up the sequence of (III)—as desired—following in order Examples 7B-7H.

The preparation is concluded by splitting of the peptides from the resin and simultaneous deprotection in two phases (Examples 7H and 7I) or one phase (Example 8G).

EXAMPLE 12

Synthesis of peptides (XXVII)-(XXXIV)

The sequential synthesis of peptide (II) is carried out in solid phase as indicated in Examples 5A-5G. Proceed with condensation of the glycine using BOC-glycine and DCCD in the same way as previously reported and continuing as required with the condensation of the asparagine and the other amino acids, as reported in Example 11, finally obtaining the desired peptides (XXVII)-(XXXIV).

EXAMPLE 13

Synthesis in homogeneous phase of peptide (V)

Add 1.79 g (5.53 mmol) of 4-benzyl ester BOC-L-aspartic acid in 20 ml of $CH_2Cl_2$ and 1.25 g (6.08 mmol) of DCCD to 2.0 g (5.53 mmol) of O-benzyl-L-tyrosine benzyl ester dissolved in 20 ml of dichloromethane, and leave under agitation at 4° C. for 18 hours.

Filter away the dicyclohexylurea formed, evaporate the filtrate in vacuum and crystallize from ethanol-$H_2O$ obtaining 3.24 g (4.87 mmol, yield=88%) of BOC-(4-benzylester)Asp-(O-benzyl)Tyr benzyl ester protected dipeptide (IVa) (TLC, Rf=0.95 in $CHCl_3$:$CH_3OH$ 95:5). 3.24 g of (IVa) are BOC-deprotected by treatment with 30 ml of $CH_2Cl_2$:TFA 1:1, 30 minutes under agitation at room temperature; evaporate the solvent in vacuum and isolate the dipeptide TFA. $NH_2$-(4-benzylester)Asp-(O-benzyl)Tyr benzyl ester (IVb) obtaining 3.21 g (4.72 mmol, Yield=97%).

Reunite 3.21 g of (IVb) dissolved in 25 ml of DMF, 0.7 ml (5 mmol) of triethylamine, 1.46 g (4.72 mmol) of BOC-O-benzyl-L-threonine in 20 ml of DMF and 1.07 g (5.19 mmol) of DCCD and keep under agitation at 4° C. for 18 hours. After filtration, evaporation of the filtrate and purification by crystallization 3.32 g (3.87 mmol) of BOC-(O-benzyl)Thr-(4-benzylester)Asp-(O-benzyl)Tyr benzyl ester protected tripeptide (Va) are obtained (Yield=82%). BOC-deprotection with $CH_2Cl_2$:TFA 1:1, gives 3.23 g (3.71 mmol) of TFA.$NH_2$-(O-benzyl)Thr-(4-benzylester)Asp-(O-benzyl)Tyr benzylester (Vb) (Yield=96%). Side chain deprotection: 3.23 g of (Vb) are dissolved in 80% aqueous acetic acid and catalytic hydrogenation carried out with 10% Pd on carbon for 60 hours at room temperature. After filtration of the catalyst, lyophilization of the filtrate, neutralization and crystallization 1.19 g (3.0 mmol) of $NH_2$-Thr-Asp-Tyr-COOH tripeptide (V) are obtained (Yield=81%). In TLC just one spot is seen (Rf=0.63 in ethanol:28% ammonia 70:30) positive to ninhydrin and Pauly's reagent.

EXAMPLE 14

Synthesis in homogeneous phase of peptide (XIX)

2.0 g (6.46 mmol) of $N_\omega$-nitro-L-arginine benzyl ester and 2.74 g (7.75 mmol) of BOC-L-asparagine p-nitrophenyl-ester dissolved in 25 ml of DMF, are kept under agitation at 4° C. for 18 hours.

Evaporate the solvent in vacuum and purify the BOC-Asn($N_\omega$-nitro)Arg benzyl ester protected dipeptide (XVIa) by chromatography on silica gel and crystallization (abs. ethanol) obtaining 2.4 g (4.72 mmol, yield 73%). TLC in $CHCl_3$:$CH_3OH$ 9:1 evidences just one spot with Rf=0.27.

2.4 g of (XVIa) are BOC-deprotected by treatment with 20 ml of $CH_2Cl_2$:TFA 1:1 mixture, 1 hour under agitation at room temperature; evaporate the solution in vacuum and isolate the TFA.$NH_2$-Asn-($N_\omega$-nitro)Arg benzyl ester dipeptide (XVIb) obtaining 2.43 g (4.64 mmol, yield=98.6%).

0.7 ml (5 mmol) of triethylamine and 2.26 g (5.57 mmol) of BOC-O-benzyl-L-threonine N-hydroxysuccinimide ester in 20 ml DMF are added to 2.43 g of (XVIb) dissolved in 30 ml DMF, leaving under agitation at 4° C. for 18 hours. After evaporation of the solvent and crystallization from ethanol 2.65 g (3.72 mmol, yield 80%) of BOC-(O-benzyl)Thr-Asn-($N_\omega$-nitro)Arg benzyl ester protected tripeptide (XVIIa) are isolated.

TLC in $CHCl_3$:$CH_3OH$:$CH_3COOH$ 90:8:2 gives a spot with Rf=0.37.

BOC-deprotection of (XVIIa) with $CH_2Cl_2$:TFA gives 2.70 g (3.71 mmol) of TFA.$NH_2$-(O-benzyl)Thr-Asn-($N_\omega$-nitro)Arg benzyl ester (XVIIb) (Yield=100%). A mixture of 2.70 g of (XVIIb) dissolved in 30 ml DMF, 0.56 ml (4.0 mmol) of triethylamine and 1.27 g (4.45 mmol) of BOC-L-alanine N-hydroxy-succinimide ester are left under agitation at 4° C. for 18 hours. 2.84 g (3.61 mmol, yield 97.4%) of BOC-Ala-(O-benzyl)Thr-Asn-($N_\omega$-nitro)Arg benzyl ester protected tetrapeptide (XVIIIa) are obtained after crystallization from abs. ethanol. TLC in $CHCl_3$:$CH_3OH$ 9:1, Rf=0.37. After BOC-deprotection 2.85 g (3.57 mmol) of TFA $NH_2$-Ala-(O-benzyl)Thr-Asn-($N_\omega$-nitro)Arg benzyl ester (XVIIIb) are obtained (Yield=98.9%).

2.85 g of (XVIIIb) dissolved in 30 ml DMF are treated with 0.56 ml (4.0 mmol) of triethylamine and 1.57 g (4.28 mmol) of BOC-L-glutamine p-nitrophenylester in 20 ml DMF and left under agitation at 4° C. for 36 hours. After crystallization, 2.99 g (3.27 mmol, yield 91.7%) of BOC-Gln-Ala-(O-benzyl)Thr-Asn-($N_\omega$-nitro)Arg benzyl ester protected pentapeptide (XIXa) are isolated. TLC in $CHCl_3$:$CH_3OH$ 9:1 Rf=0.17. After BOC-deprotection, 3.03 g (3.27 mmol) of TFA.$NH_2$-Gln-Ala-(O-benzyl)Thr-Asn-($N_\omega$-nitro)Arg benzyl ester (XIXb) are obtained (Yield 100%).

Side chain deprotection: 3.03 g of (XIXb) are dissolved in 100 ml of 80% aqueous acetic acid and catalytic hydrogenation carried out with 10% Pd on carbon for 48 hours at room temperature. The catalyst is removed by filtration and the filtrate lyophilized. After neutralization with triethylamine and purification by crystallization, 1.50 g of $NH_2$-Gln-Ala-Thr-Asn-Arg-COOH pentapeptide (XIX) are isolated (Yield 78%). TLC shows just one spot (Rf=0.19 in methanol:28% ammonia 9:1) positive to ninhydrin and Sakaguchi's reagent.

We claim:

1. A peptide selected from the group consisting of:

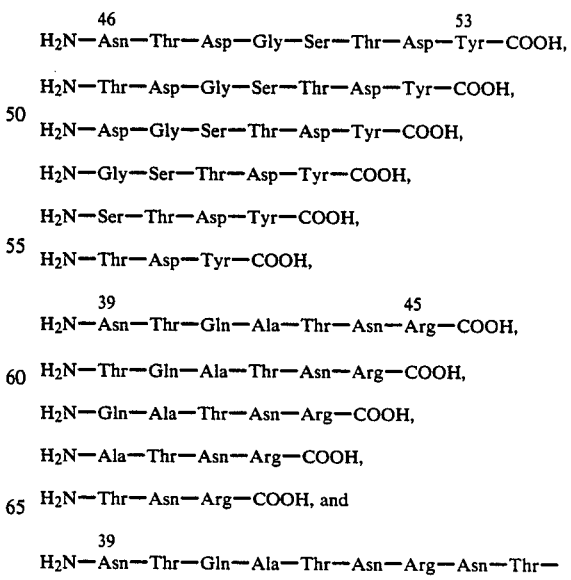

$\overset{46}{H_2N}$—Asn—Thr—Asp—Gly—Ser—Thr—Asp—$\overset{53}{Tyr}$—COOH, $H_2N$—Thr—Asp—Gly—Ser—Thr—Asp—Tyr—COOH, $H_2N$—Asp—Gly—Ser—Thr—Asp—Tyr—COOH, $H_2N$—Gly—Ser—Thr—Asp—Tyr—COOH, $H_2N$—Ser—Thr—Asp—Tyr—COOH, $H_2N$—Thr—Asp—Tyr—COOH, $\overset{39}{H_2N}$—Asn—Thr—Gln—Ala—Thr—Asn—$\overset{45}{Arg}$—COOH, $H_2N$—Thr—Gln—Ala—Thr—Asn—Arg—COOH, $H_2N$—Gln—Ala—Thr—Asn—Arg—COOH, $H_2N$—Ala—Thr—Asn—Arg—COOH, $H_2N$—Thr—Asn—Arg—COOH, and $\overset{39}{H_2N}$—Asn—Thr—Gln—Ala—Thr—Asn—Arg—Asn—Thr—

—Asp—Gly—Ser—Thr—Asp—Tyr—COOH.

2. The peptide of claim 1, which is: H₂N-Asn-Thr-Asp-Gly-Ser-Thr-Asp-Tyr-COOH.

3. The peptide of claim 1, which is: H₂N-Thr-Asp-Gly-Ser-Thr-Asp-Tyr-COOH.

4. The peptide according to claim 1, which is: H₂N-Asp-Gly-Ser-Thr-Asp-Tyr-COOH.

5. The peptide according to claim 1, which is: H₂N-Gly-Ser-Thr-Asp-Tyr-COOH.

6. The peptide according to claim 1, which is: H₂N-Ser-Thr-Asp-Tyr-COOH.

7. The peptide according to claim 1, which is: H₂N-Thr-Asp-Tyr-COOH.

8. The peptide according to claim 1, which is: H₂N-Asn-Thr-Gln-Ala-Thr-Asn-Arg-COOH.

9. The peptide according to claim 1, which is: H₂N-Thr-Gln-Ala-Thr-Asn-Arg-COOH.

10. The peptide according to claim 1, which is: H₂N-Gln-Ala-Thr-Asn-Arg-COOH.

11. The peptide according to claim 1, which is: H₂N-Ala-Thr-Asn-Arg-COOH.

12. The peptide according to claim 1, which is: H₂N-Thr-Asn-Arg-COOH.

13. The peptide according to claim 1, which is: H₂N-Asn-Thr-Gln-Ala-Thr-Asn-Arg-Asn-Thr-Asp-Gly-Ser-Thr-Asp-Tyr-COOH.

14. A pharmaceutical formulation having analgesic, antiviral or immunomodulating activity, which comprises an effective amount of a peptide according to claim 1, in combination with a pharmaceutically acceptable carrier.

* * * * *